United States Patent [19]

Gähwiler

[11] Patent Number: 4,465,476

[45] Date of Patent: Aug. 14, 1984

[54] INJECTION SYRINGE FOR INJECTING TWO LIQUIDS

[75] Inventor: Hermann Gähwiler, Zürich, Switzerland

[73] Assignee: Contraves AG, Zürich, Switzerland

[21] Appl. No.: 448,705

[22] Filed: Dec. 10, 1982

[30] Foreign Application Priority Data

Dec. 22, 1981 [CH] Switzerland ............... 8184/81

[51] Int. Cl.³ ............................................. A61M 1/00
[52] U.S. Cl. ............................................. 604/191
[58] Field of Search ............... 604/191, 183, 184, 218, 604/220, 228; 128/654, 655

[56] References Cited

U.S. PATENT DOCUMENTS

| | | |
|---|---|---|
| 3,685,514 | 8/1972 | Cheney . |
| 3,910,273 | 10/1975 | Arlers ............... 604/228 |
| 3,957,051 | 5/1976 | Topham ............... 604/191 |
| 3,985,122 | 10/1976 | Topham ............... 604/191 |

FOREIGN PATENT DOCUMENTS

| | | |
|---|---|---|
| 730362 | 1/1943 | Fed. Rep. of Germany . |
| 440560 | 7/1967 | Switzerland . |
| 445721 | 10/1967 | Switzerland . |
| 580427 | 8/1976 | Switzerland . |
| 1214053 | 12/1970 | United Kingdom . |

*Primary Examiner*—John D. Yasko
*Attorney, Agent, or Firm*—Werner W. Kleeman

[57] ABSTRACT

The injection syringe for injecting two liquids has a cylinder within which there are displaceably arranged in a liquid-tight fashion a piston as well as a separator piston member. The separator piston member divides the internal space of the cylinder into a first front compartment and a second rear compartment and is provided with a spacer rod arranged to be displaced in a liquid-tight fashion within a bore of the piston. Retaining or holder means ensure that the separator piston member maintains a constant spacing from the piston while the first liquid in the first front compartment is being ejected, whereas the separator piston member and the piston are displaceable relative to each other during ejection of the second liquid. The dual-liquid injection syringe is particularly utilized in computerized tomography for injecting a contrast medium and a flushing medium.

16 Claims, 6 Drawing Figures

INJECTION SYRINGE FOR INJECTING TWO LIQUIDS

CROSS-REFERENCE TO RELATED APPLICATION

This application is related to the commonly assigned, copending U.S. application Ser. No. 436,307, filed Oct. 25, 1982, entitled "Injection Syringe For The Successive Injection Of Two Liquids Into The Blood Vessels Of Living Bodies".

BACKGROUND OF THE INVENTION

The present invention relates to a new and improved construction of an injection syringe, also simply referred to as a syringe, for the successive injection of two liquids or agents into the blood vessels of living bodies or the like.

In its more particular aspects, the syringe for the successive injection of two liquids, especially although not exclusively, a liquid contrast agent or medium and a flushing agent or medium, into the blood vessels of living bodies, is of the type comprising a cylinder provided at one end thereof with an attachment or connection flange and at the other end thereof contains, at the region of an outlet or discharge opening, a catheter connection or equivalent structure. A piston member can be inserted into the cylinder, so as to be displaceable therein in a liquid-tight manner.

Particularly in the field of computer tomography an injection technique is gaining increasing importance, wherein immediately after injecting a contrast medium there is injected a physiological saline or salt solution. However, with the state-of-the art syringes, for instance as disclosed in Swiss Patent No. 580,427, granted Aug. 31, 1976, there only can be injected during one working operation a single liquid. Thus, there must be employed in each case two syringes, each of which is filled with a respective liquid and each of which is provided with a respective drive. Apart from the high costs involved with the employment of two syringes and two drives the use of two systems requires a correspondingly greater expenditure in terms of servicing and operating the same as well as monitoring such systems.

SUMMARY OF THE INVENTION

Therefore, with the foregoing in mind it is a primary object of the present invention to provide an improved construction of syringe for the successive injection of two liquids in a manner which is not afflicted with the aforementioned drawbacks and limitations of the prior art proposals.

Another and more specific object of the present invention aims at the provision of a new and improved construction of a syringe of the aforementioned type, by means of which it is possible to effectively inject in succession two liquids, and wherein there are effectively complied with the high requirements as concerns reliability and accuracy which are placed upon such medical equipment.

Still a further significant object of the present invention is directed to a new and improved construction of a syringe for the successive injection of two liquids, which syringe is relatively simple in construction and design, quite economical to manufacture, extremely easy to use, and not readily subject to breakdown or malfunction.

Now in order to implement these and still further objects of the invention, which will become more readily apparent as the description proceeds, the syringe of the present development is manifested by the features, that there is provided a separator piston member which is disposed in the cylinder intermediate the piston and the outlet or discharge opening to separate the two liquids. A spacer rod extends substantially in parallelism with respect to the cylinder axis and is mounted at the separator piston member. Retaining means serve to hold the spacer rod in an axial bore of the piston during ejection of the first liquid, and the spacer rod is movable in a liquid-tight fashion in the axial bore during ejection of the second liquid.

The retaining or holder means may be structured as locking or latching means comprising at least one locking spring mounted in a counterbore of the piston, and there is provided at least one detent at the locking spring, said detent latching into a recess formed at the circumference of the spacer rod.

The separator piston member of the injection syringe according to the invention may have a convexly, preferably conically-shaped front face and a convexly, preferably conically-shaped rear face. The front face may be shaped so as to be adapted to the shape of the syringe cylinder at the outlet region thereof.

According to another aspect of the invention the separator piston member comprises a flexible plate at the end of the spacer rod which is remote from the piston. An annular support is provided for the flexible plate at the circumference thereof. A central closure member is arranged at the end of the spacer rod remote from the piston in order to closingly engage the plate.

In the injection syringe according to the invention, the first liquid is ejected from the first compartment by movement of the piston in conjunction with the separator piston member until the latter contacts the outlet end of the syringe cylinder. Subsequently, the second liquid is ejected from the second compartment by movement of the piston relative to the separator piston member after surmounting the resistance against such movement as provided, for example, by the locking means mentioned heretofore. In the case where the separator piston member includes a flexible plate, this flexible plate remains in closing engagement with the central closure member on the spacer rod as long as there is no pressure difference acting upon the flexible plate. After the first liquid has been ejected, the axial pressure on the piston produces a pressure difference at the flexible plate which, then, disengages from the closure member, so that the second liquid may be discharged through the outlet of the syringe.

BRIEF DESCRIPTION OF THE DRAWINGS

The invention will be better understood and objects other than those set forth above, will become apparent when consideration is given to the following detailed description thereof. Such description makes reference to the annexed drawings wherein.

DETAILED DESCRIPTION OF THE PREFERRED EMBODIMENTS

Figure 1:
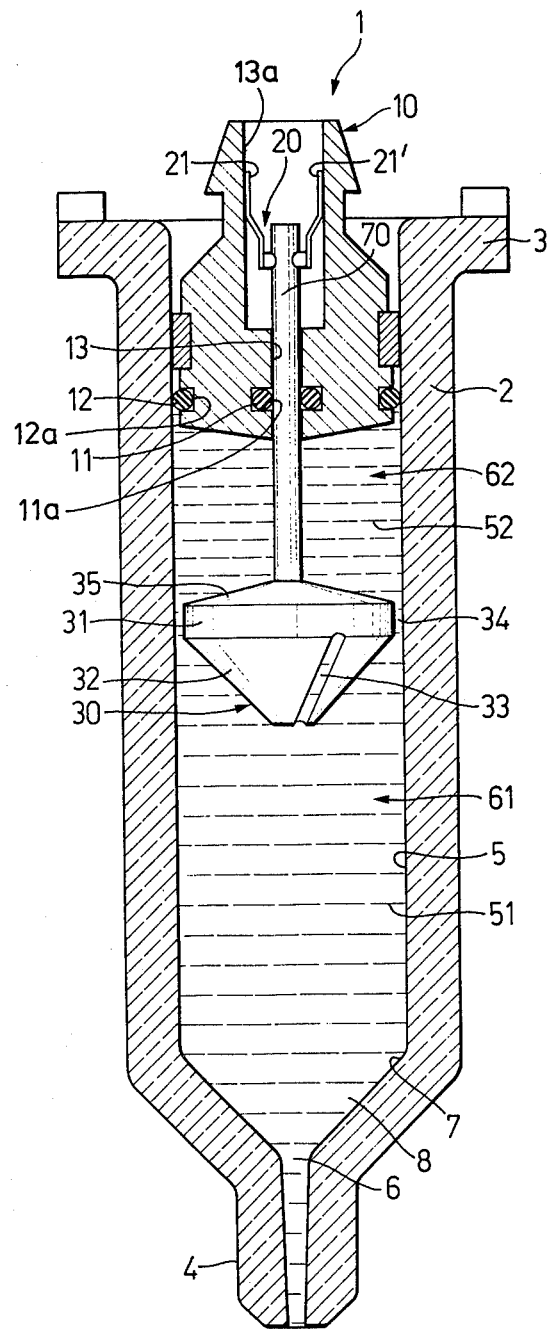
FIG. 1 is a view, partially in section, illustrating the injection syringe according to the invention in a state prior to injection of the two liquids.

Describing now the drawings, it is to be understood that in order to simplify the illustration only enough of the construction of the injection syringe has been shown as needed for those skilled in the art to readily understand the underlying principles and concepts of the present invention. Turning attention now specifically to the drawing of FIG. 1, there is shown an injection syringe 1 comprising a cylinder 2, a piston or piston member 10 displaceable in the cylinder 2, a mounting flange 3 at the upper end of the cylinder 2, an outlet or discharge opening 6 at the lower end of the cylinder 2, and a connecting member 4 for connection to a catheter or the like (not shown). Into the internal space or chamber of the cylinder 2 of the injection syringe there is inserted the piston 10 and such is sealingly guided by a sealing ring 12 received in an annular groove 12a provided at the circumference of this piston or piston member 10 which is mounted for slideable axial movement within the cylinder 2.

The piston or piston member 10 has an axial bore 13 through which piercingly extends a spacer rod 70. A sealing ring 11 is accommodated in an annular groove 11a formed in the internal axial bore 13 of the piston 10, so that this piston 10 and the spacer rod 70 are movable in a liquid-tight fashion with respect to each other in axial direction. The spacer rod 70 passes through the internal axial bore 13 in the piston or piston member 10 and has a free end at which there is secured a separator member 30, here a separator piston member. The separator piston member 30 contains a substantially conical front face 32, a substantially conical rear face 35 and a substantially cylindrical face 31. A small cylindrical or annular gap 34 exists between the cylindrical face 31 of the separator piston member 30 and the inner cylindrical wall 5 of the syringe cylinder 2. The cylindrical gap 34 thus formed has a small width, for example, in the range of about 1 mm and has an axial length, for example, of about 15 mm, so that the admixing of both liquids 51 and 52 is negligibly small. By means of the separator piston member 30 two compartments 61 and 62 are formed within the cylinder 2, the first compartment 61 of which is defined by the outlet 6 and the front face 32 of the separator piston member 30, and the second compartment of which is defined by the rear face 35 of the separator piston member 30 and the front face of the piston or piston member 10.

The spacer rod 70 is retained by locking means 20 in a counterbore 13a formed at the end of the piston or piston member 10 which is remote from the separator piston member 30. The locking or latching means 20, for example, may comprise two locking or latching springs 21 and 21', each having a locking detent or nose 22 and 22', respectively. The locking detents 22 and 22' are shown in engagement with associated recesses 23 and 23', respectively, formed at the circumference or outer surface of the spacer rod 70.

Another possibility of securing the separator piston member 30 against axial displacement at the piston or piston member 10 during ejection of the first liquid 51 from the first compartment 61 may be obtained by providing for sufficiently high friction between the spacer rod 70 and the piston 10 within the axial bore 13. This can be achieved, for example, by providing a sufficiently narrow bore 13. This has the advantage that the distance of the separator piston member 30 from the piston 10 may be continuously varied, whereby the volume of the rear compartment 62 becomes variable.

In the drawing of FIG. 1, the injection syringe according to the invention is shown in a state ready for the successive injection of the two liquids 51 and 52. The first liquid 51, which may be, for example, a contrast agent or medium, is located within the front compartment 61, while the second liquid 52, which may be, for example, a flushing agent or medium is present in the rear compartment 62.

For injection of the first liquid 51 the piston member 10 and the separator piston member 30 are conjointly displaced in a direction towards the outlet 6 until the front conical face 32 of the separator piston member 30 abuts against the conically-shaped bottom or base region 8 of the cylinder 2. The separator piston member 30 is still retained at a constant spacing from the piston member 10 by means of the spacer rod 70. As mentioned previously, the size or dimension of the cylindrical or annular gap 34 between the cylindrical wall 31 of the separator piston member 30 and the inner wall 5 of the cylinder 2 is appropriate to prevent any appreciable intermixing of the two different liquids 51 and 52 present in the compartments 61 and 62, respectively. In this state, when the separator piston member 30 abuts against the bottom 8 of the cylinder 2, the first liquid 51 has been ejected, whereas the second liquid 52 is still present completely within the rear compartment 62.

Figure 2:
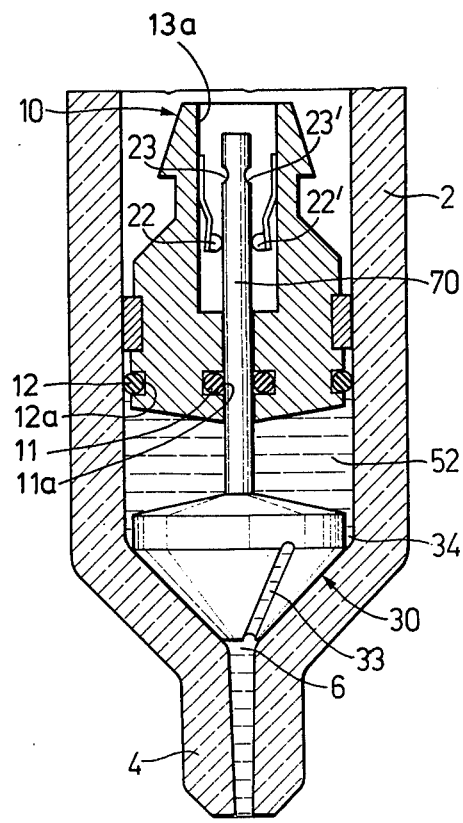
FIG. 2 is a view of the injection syringe shown in FIG. 1 in a state of injection of the second liquid contained in the syringe cylinder and following injection of the first liquid.
Figure 3:
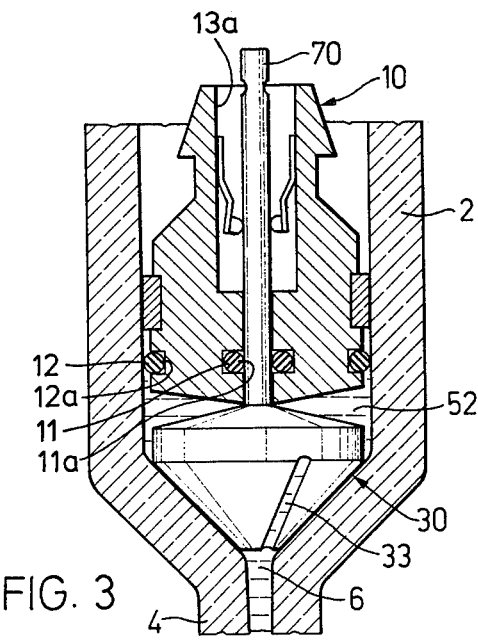
FIG. 3 is a view similar to that shown in FIG. 2 depicting the injection syringe in a final state after termination of the injection.

Now to inject the second liquid 52 the spacer rod 70 is released from the locking means 20 by exerting an increased pressure upon the piston member 10. Consequently, the locking springs 21 and 21' are released or delatched from the recesses 23 and 23', respectively. The piston member 10, then, may be displaced relative to the separator piston member 30. By advancement of the piston member 10 the second liquid 52 is ejected through the cylindrical or annular gap 34 towards the outlet 6. FIG. 2 shows the inventive injection syringe in a state where the first liquid 51 has been completely ejected while the second liquid 52 has been only partially ejected. FIG. 3 shows the injection syringe according to the invention in a final state, in which both the first liquid 51 and second liquid 52 have been ejected from the injection syringe 1.

To ensure passage of the second liquid 52 after ejection of the first liquid 51 there are beneficially provided flow channels 33 at the front conical face 32 of the separator piston member 30. It has been found, however, particularly in the case of a physiological salt solution which is used as a flushing medium and which is contained in the second compartment 52, that a separator piston member having no flow channels 33 also may be utilized and does not cause any blockage at the region of the discharge opening or outlet 6.

Figure 4:
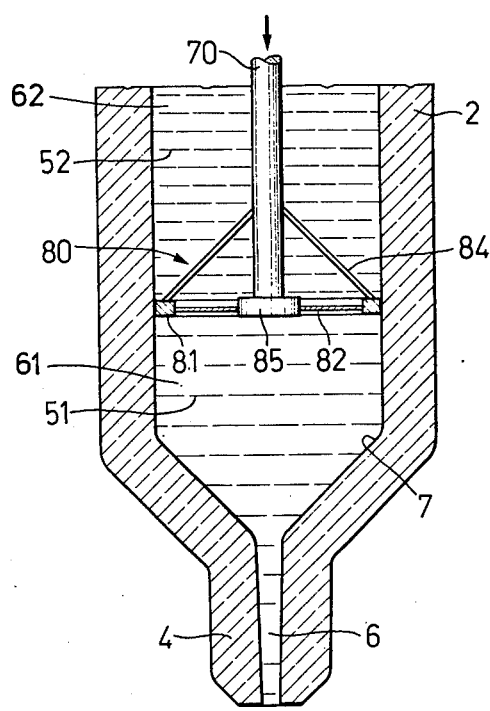
FIG. 4 is a sectional view of part of an injection syringe according to the invention which is equipped with a modified separator piston member and which is in a state of injection of the first liquid from the syringe cylinder.
Figure 5:
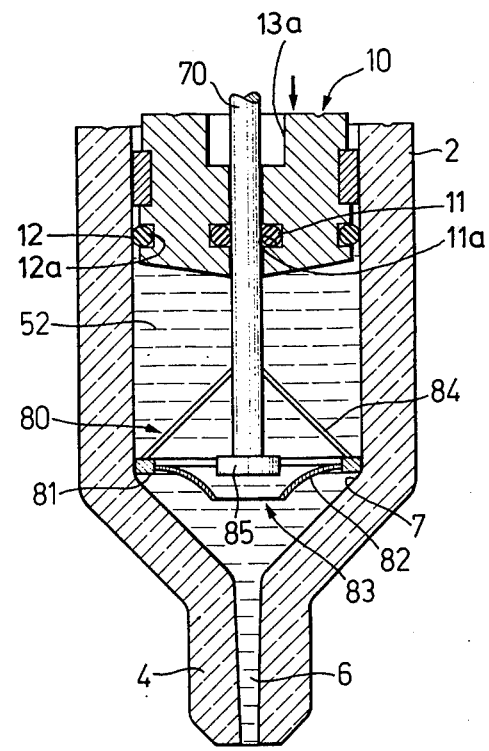
FIG. 5 is a sectional view of the injection syringe shown in FIG. 4 in a state of injection of the second liquid from the syringe cylinder.
Figure 6:
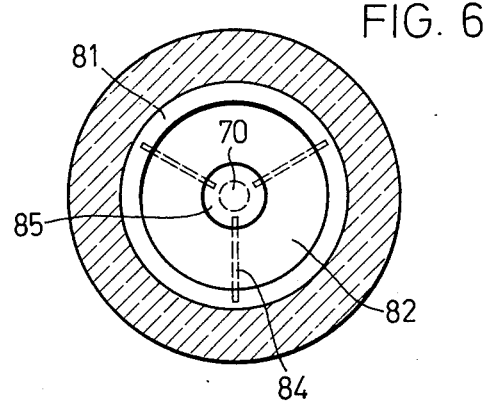
FIG. 6 is a top plan view of the injection syringe shown in FIG. 4 and including the modified separator piston member.

FIGS. 4 to 6 of the drawings show a modified construction of an injection syringe for the successive injection of the two liquids 51 and 52 and which is equipped with a modified separator piston member 80. Otherwise, the injection syringe is essentially constructed the same as that shown in FIGS. 1 to 3, and thus, corresponding parts have been conveniently designated by generally using the same reference numerals. For simplicity, the drawings of FIGS. 4 to 6 show only those parts of the injection syringe which include the modified version of the separator piston member 80.

The separator piston member 80 will be seen to comprise a support ring 81, a flexible plate or lamellae 82 mounted thereto, and a central closure member 85 mounted at the spacer rod 30. The support ring 81 is retained at the spacer rod 70 by means of lateral struts 84 of which, for example, three are provided. During ejection of the first liquid 51, the flexible plate 82 or equivalent structure remains in the closed position due to the pressure equilibrium in both the front compartment 61 and the rear compartment 62. When the support ring 81 abuts a front cylindrical surface or edge 7 of the cylinder 2 and the pressure in the rear compartment 62 is increased, the flexible plate or lamellae 82 will automatically open, so that the second liquid 52 will pass through an opening 83 which is thus formed during further movement of the piston or piston member 10.

FIG. 6 shows a top plan view in axial direction of the separator piston member 80 shown in FIG. 4. The support ring 81, to which the circular flexible plate 82 is secured, will be clearly evident. The opening 83 in the plate 82 is closed in a plug-like manner by the closure member 85.

In the following description the filling of the inventive injection syringes with the two liquids 51 and 52 will be explained in greater detail. While the discussion will be made with reference to the syringe of FIGS. 1 to 3, it is analogously applicable to the modified syringe construction of FIGS. 4 to 6.

The empty syringe cylinder 2 is closed near the outlet 6 and completely filled with the second liquid 52 which may be, for example, a physiological salt solution which is to be subsequently injected. Then, the piston member 10, including the separator piston member 30 in its most extended or desired spaced position, is slowly introduced. The liquid passes through the cylindrical or annular gap 34 formed between the separator piston member 30 and the inner wall 5 of the cylinder 2 so as to fill the rear compartment 62. The slightly conical shape of the rear face 35 of the separator piston member 30 and the slightly conical shape of the front face 32 of the separator piston member 30 facilitate the filling operation which is to be performed with the exclusion of air. The resistance to the introduction of the piston member 10 strongly increases when the piston member 10 has become axially introduced to such an extent that the sealing ring 12 of the piston member 10 contacts the inner wall 2. The cylinder 2 is now reopened at the front end at the outlet 6 and the piston member 10 is then advanced by about 1 centimeter, and then, the cylinder 2 is connected to an injector. The front compartment 61 is then emptied of the remaining second liquid 52 by correspondingly advancing the piston member 10, and thereafter a contrast agent or medium is sucked-up through the outlet 6 into the first compartment 61 by retracting the piston member 10.

While there are shown and described present preferred embodiments of the invention, it is to be distinctly understood that the invention is not limited thereto, but may be otherwise variously embodied and and practiced within the scope of the following claims. Accordingly,

What I claim is:

1. An injection syringe for the successive injection of two liquids into the blood vessels of living bodies, comprising:
    a cylinder having opposed ends and a cylinder axis;
    one of said opposed ends of said cylinder defining an outlet end containing an outlet opening;
    a piston insertable into said cylinder and slidably movable within said cylinder;
    said piston having an axial bore;
    a separator piston member disposed in said cylinder intermediate said piston and said outlet opening to subdivide the cylinder into two separate compartments each holding one of the two liquids in the filled state of said cylinder;
    a spacer rod extending substantially in parallelism to said cylinder axis and arranged at said spearator piston member;
    retaining means for releasably holding said spacer rod at said piston; and
    said piston, after ejection of a first one of the two liquids and automatic release of said retaining means, being movable in a substantially liquid-tight manner relative to said spacer rod in order to eject a second one of the two liquids.

2. The injection syringe as defined in claim 1, wherein:
    said separator piston member has a convex-shaped front face facing said outlet opening and a convex-shaped rear face facing said piston.

3. The injection syringe as defined in claim 2, wherein:
    said convex-shaped front face is of substantially conical shape.

4. The injection syringe as defined in claim 2, wherein:
    said convex-shaped rear face is of substantially conical shape.

5. The injection syringe as defined in claim 1, wherein:
    said separator piston member cooperates with an inner wall of said cylinder to form therebetween a narrow substantially cylindrical gap.

6. The injection syringe as defined in claim 1, wherein:
    said retaining means comprise at least one locking spring.

7. The injection syringe as defined in claim 1, further including:
    an elastic plate provided for said separator piston member; and
    said elastic plate being closed in a substantially liquid-tight fashion during ejection of said first one of said two liquids and being structured to form an opening during ejection of said second one of said two liquids.

8. The injection syringe as defined in claim 1, further including:
    means for frictionally holding said spacer rod in said axial bore of said piston.

9. The injection syringe as defined in claim 1, wherein:
    said piston has a counterbore at an end thereof remote from said separator piston member; and locking means disposed in said counterbore for releasably retaining said spacer rod in said counterbore.

10. An injection syringe for the successive injection of two liquids into the blood vessels of living bodies, comprising:
- a cylinder having opposed ends and a cylinder axis;
- one of said opposed ends of said cylinder defining an outlet end containing an outlet opening;
- a piston insertable into said cylinder and movable within said cylinder;
- said piston having an axial bore;
- a separator piston member disposed in said cylinder intermediate said piston and said outlet opening to separate the two liquids;
- a spacer rod extending substantially in parallelism to said cylinder axis and arranged at said separator member;
- retaining means for holding said spacer rod in said axial bore of said piston during ejection of a first one of said two liquids;
- said spacer rod being movable in a substantially liquid-tight fashion in said axial bore of said piston during ejection of a second one of said two liquids;
- said piston having a counterbore at an end thereof remote from said separator piston member;
- locking means disposed in said counterbore for releasably retaining said spacer rod in said counterbore;
- said locking means comprising:
- at least one locking spring mounted in said counterbore;
- at least one detent formed at said at least one locking spring;
- at least one recess formed at the circumference of said spacer rod; and
- said at least one detent and said at least one recess coactingly lockingly interengaging with one another in a predetermined locking position where said spacer rod is locked against axial movement relative to said piston.

11. The injection syringe as defined in claim 1, wherein:
- said separator piston member comprises a flexible plate at an end of said spacer rod which is remote from said piston;
- a support ring secured to said spacer rod to support said flexible plate at the circumference thereof;
- mounting means for mounting said support ring at said spacer rod;
- a central closure member provided at said end of said spacer rod which is remote from said piston for sealingly engaging said flexible plate as long as substantially no pressure difference acts upon the same.

12. The injection syringe as defined in claim 11, wherein:
- said mounting means comprise struts extending from said support ring to said spacer rod.

13. An injection syringe for the successive injection of two liquids into the blood vessels of living bodies, comprising:
- a cylinder having opposed ends and a cylinder axis;
- one of said opposed ends of said cylinder defining an outlet end containing an outlet opening;
- a piston in a substantially liquid-tight manner insertable into said cylinder and movable within said cylinder;
- said piston having an axial bore;
- a separator piston member disposed in said cylinder intermediate said piston and said outlet opening to subdivide the cylinder into two separate compartments each holding one of the two liquids in the filled state of said cylinder;
- passage means provided at said separator piston member;
- said passage means effectively separating said two liquids from each other to prevent intermixing thereof;
- a spacer rod having one end arranged at said separator piston member and substantially in a liquid-tight manner extending substantially in parallelism to said cylinder axis through said piston a second end thereof;
- automatically releasable retaining means for holding said second end of said spacer rod at said piston;
- said piston, said spacer rod and said separator piston member being conjointly movable towards said outlet opening of said cylinder in order to eject the first one of said two liquids; and
- said piston subsequently being further movable towards said outlet opening of said cylinder and, after automatic release from said retaining means, relative to said spacer rod and to said separator piston member in order to force the second one of said two liquids through said passage means and to eject the same.

14. The injection syringe as defined in claim 13, wherein:
- said cylinder comprising an inner wall;
- said separator piston member having a substantially cylindrical portion; and
- said passage means comrpising a narrow substantially cylindrical gap formed between said substantially cylindrical portion and said inner wall of said cylinder.

15. The injection syringe as defined in claim 14, wherein:
- said separator piston member comprises a convex-shaped front face facing said outlet opening of said cylinder; and
- said passage means further comprising a number of flow channels radially extending from said substantially cylindrical portion of said separator piston member on said convex-shaped front face thereof.

16. The injection syringe as defined in claim 13, wherein:
- said passage means comprise an elastically deformable plate mounted at said separator piston member;
- said elastically deformable plate being arranged at said separator or piston member in a substantially liquid-tight closed state during ejection of the first one of the two liquids; and
- said elastically deformable plate subsequently being automatically deformable to provide an opening for the through-flow of the second one of the two liquids during ejection thereof.

* * * * *